(12) United States Patent
Carson et al.

(10) Patent No.: US 9,090,033 B2
(45) Date of Patent: Jul. 28, 2015

(54) PRESBYOPIA-CORRECTING IOL USING CURVATURE CHANGE OF AN AIR CHAMBER

(71) Applicant: NOVARTIS AG, Basel (CH)

(72) Inventors: Daniel R. Carson, Fort Worth, TX (US); Shinwook Lee, Arlington, TX (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/094,995

(22) Filed: Dec. 3, 2013

(65) Prior Publication Data

US 2014/0172092 A1    Jun. 19, 2014

Related U.S. Application Data

(60) Provisional application No. 61/738,853, filed on Dec. 18, 2012.

(51) Int. Cl.
*A61F 2/16* (2006.01)
*B29D 11/02* (2006.01)

(52) U.S. Cl.
CPC ............ *B29D 11/023* (2013.01); *A61F 2/1624* (2013.01); *A61F 2/1635* (2013.01); *A61F 2/1648* (2013.01)

(58) Field of Classification Search
CPC .............................. A61F 2/1624; A61F 2/1635
USPC ................................. 623/6.13, 6.37, 6.39, 6.4
See application file for complete search history.

(56) References Cited

U.S. PATENT DOCUMENTS

| | | | |
|---|---|---|---|
| 4,704,122 A | 11/1987 | Portnoy | |
| 4,892,543 A * | 1/1990 | Turley | 623/6.13 |
| 5,489,302 A | 2/1996 | Skottun | |
| 6,473,238 B1 | 10/2002 | Daniell | |
| 6,785,061 B2 | 8/2004 | Smith | |
| 2004/0082993 A1* | 4/2004 | Woods | 623/6.37 |
| 2005/0107873 A1 | 5/2005 | Zhou | |
| 2005/0131535 A1* | 6/2005 | Woods | 623/6.37 |
| 2006/0253196 A1 | 11/2006 | Woods | |
| 2007/0050024 A1 | 3/2007 | Zhang | |
| 2007/0100445 A1* | 5/2007 | Shadduck | 623/6.37 |
| 2007/0129799 A1 | 6/2007 | Schedler | |
| 2007/0156236 A1 | 7/2007 | Stenger | |

OTHER PUBLICATIONS

PCT/US13/72746, International Search Report, International Searching Authority, Feb. 7, 2014, 2 pgs.
PCT/US13/72746, Written Opinion, International Searching Authority, Feb. 7, 2014, 4pgs.
Pepose, "Design Strategies for New Accommodating IOLs", Cat. Refr. Surg. Today, Jan. 2009, 37-45, 7pgs.

* cited by examiner

*Primary Examiner* — David H Willse
*Assistant Examiner* — Javier Blanco
(74) *Attorney, Agent, or Firm* — Jason Finch

(57) ABSTRACT

An accommodative intraocular lens (IOL) system is disclosed for insertion into an eye to provide accommodative vision, the system including a deformable air chamber filled with a transparent, low refractive index medium disposed between the first and second optics; and at least one haptic connected to the air chamber and configured to facilitate a change in the curvature of at least one surface of the chamber, such that when the lens system is positioned in an eye, cilliary muscle movements can alter the curvature of the air chamber and vary the overall lens power of the system.

8 Claims, 3 Drawing Sheets

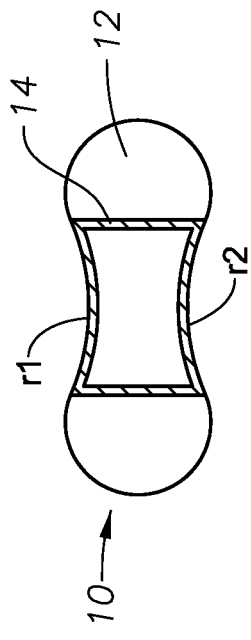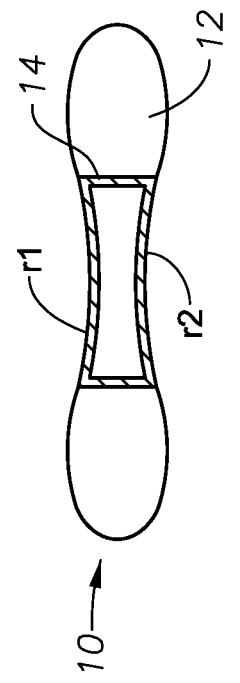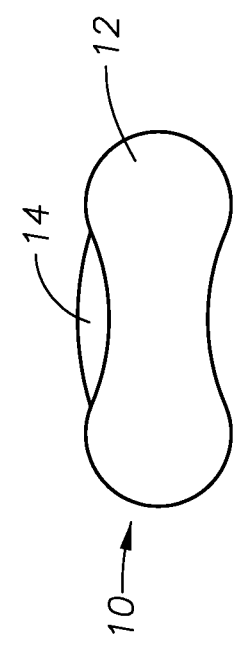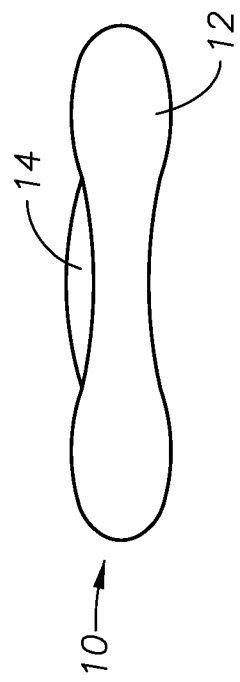

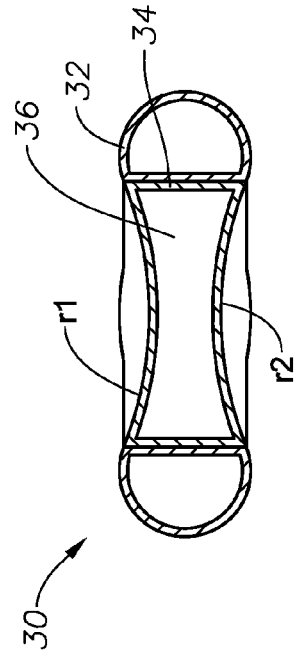
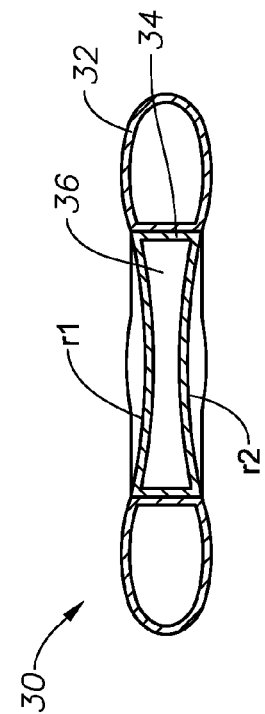
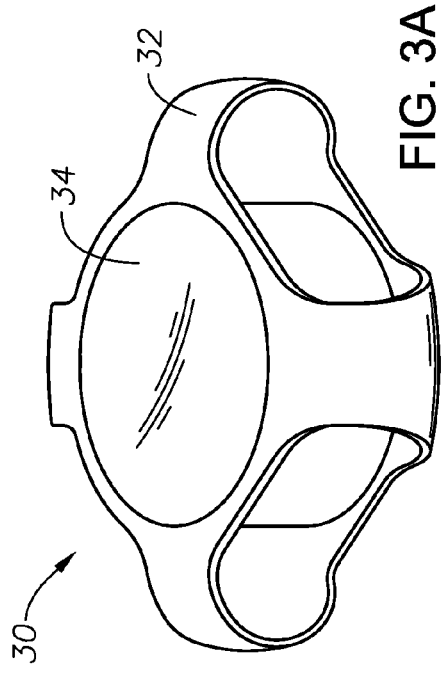
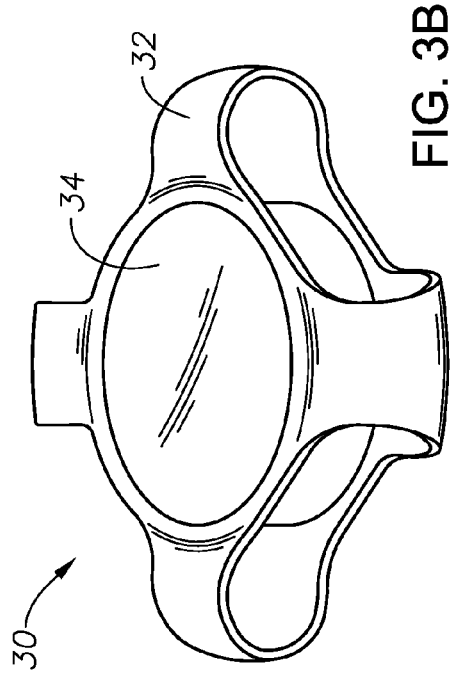

PRESBYOPIA-CORRECTING IOL USING CURVATURE CHANGE OF AN AIR CHAMBER

This application claims the priority of U.S. Provisional Patent Application No. 61/738,853 filed on Dec. 18, 2012.

TECHNICAL FIELD

This invention relates generally to the field of intraocular lenses (IOL) and, more particularly, to accommodative IOLs.

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

Cataractous lenses may be removed by a surgical technique called phacoemulsification. During this procedure, an opening is made in the anterior capsule and a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by the zonules. Relaxation of the ciliary muscle tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus alternatively on near and far objects.

As the lens ages, it becomes harder and is less able to change shape in reaction to the tightening of the ciliary muscle. This makes it harder for the lens to focus on near objects, a medical condition known as presbyopia. Presbyopia affects nearly all adults over the age of 45 or 50.

Prior art accommodative two lens systems using a movable "zoom" lens have inherently limited movement. The maximum sensitivity or movement magnification a (a unitless ratio) is defined as the axial movement of the lens per unit zonule movement and is derived by the following equation:

$$a = -B/A$$

where B is the projected distance of the zonule length which is in the order of 1.0 to 2.0 mm; and A is the axial distance between the middle plane of the dual lenses and the anterior surface of the anterior lens where the zonules terminate.

U.S. Patent Application Pub. No. US2007/0050024, the entire contents of which are incorporated herein by reference, discloses the use of a cam mechanism to increase the range of relative movement between the elements of a two-optic system. However, even with a cam element or other mechanism for increasing the range of movement in dual optic systems, it is difficult to obtain an accommodative amplitude that would restore the normal accommodation of a healthy eye, e.g., a power shift on the order of 4 diopters, due to the refractive limitations of conventional lens materials and the limited space available within the capsule. Consequently, patients can have refractive errors after the implantation of the IOL and still need additional spectacles corrections that are not desired.

Accordingly, there exists a need for better solutions to the problem of accommodation in IOLs. In particular, a single optic accommodative lens that could mimic the natural (young) lens and provide greater accommodative amplitude would satisfy a long-felt need in the field.

SUMMARY OF THE INVENTION

To overcome the above and other drawbacks of conventional systems, the present invention provides an intraocular lens (IOL) for insertion into an eye to provide accommodative vision, the system including an air chamber of variable curvature such that when the IOL is positioned in an eye, cilliary muscle movements can alter the curvature of the air chamber and vary the overall lens power of the system.

The term "air chamber" as used herein is intended to encompass a chamber filled with transparent medium with a low index of refraction. To enhance the accommodative effect of the IOL, the air chamber is filled with transparent medium that has an index of refraction less than that of the aqueous humor, e.g., between 1.4 and 1.0, preferably less than about 1.34, more preferably less than about 1.2 or 1.1, in order to provide a greater range of accommodation.

In certain embodiments, the transparent medium can be a gas, such as air. In some instances, it can be useful to use an inert gas such as argon, which also has a lower permeability vis-à-vis a sealing enclosure due, at least in part, to its higher molecular weight. Thus, the transparent medium can, for example, be composed by weight (or by volume) of at least 80% or 85%, or 90% or 95% or even 98% percent or higher of argon gas. In other applications, other fluids, e.g., liquids or gases, can be used so long as the index refraction is lower than that of the ambient ocular environment. For simplicity of description, any reservoir of a low refractive index medium that provides refractive power is referred to as an "air chamber," regardless of the actual medium contained therein.

In certain embodiments, the IOL is a single optic structure that simply relies solely on the refractive properties of the shaped air chamber. In other embodiments, the IOL can also include other lens elements in addition to the air chamber, e.g., an anterior lens (closer to the cornea or front of the eye) or a posterior lens (closer to the retina or back of the eye) or both an anterior and a posterior lens, each of which can contribute along with the air chamber to the overall power of the IOL.

One or more haptics can also be used to help transmit forces exerted by the cilliary muscle to air chamber to change the shape of the chamber (and its optical power). Moreover, the haptic or system can further include force amplifying elements, such one or more lever arms that translate the forces applied by the cilliary muscle into relative movement of one or more of the optics along the optical axis of the lens system to provide as desired level of accommodation, e.g., preferably at least about 3 diopters, or more preferably at least about 4 diopters in an eye.

In another aspect of the invention, methods of restoring accommodation in an eye are disclosed in which an IOL is provided having a deformable air chamber. The methods include a step of positioning the IOL in an eye in a manner whereby changes in a cilliary muscle will be transmitted to the system such that cilliary muscle movements alter the shape of the air chamber and thereby vary the overall lens power of the system.

In yet another aspect of the invention, methods of manufacturing accommodative intraocular lens systems are disclosed by providing a deformable air chamber filled with a transparent, low refractive index medium. The manufacturing method can further include the step of joining the air chamber to a flexible haptic configured to translate lateral forces into a deformation of the air chamber, whereby when the IOL is positioned in an eye, changes in the position of the cilliary muscle will be transmitted to the system such that cilliary muscle movements alter the curvature of one or more surfaces of the air chamber.

BRIEF DESCRIPTION OF THE DRAWINGS

The invention will be more fully understood from the following detailed description taken in conjunction with the accompanying drawings, in which:

FIG. 1A is a perspective schematic illustration of an accommodative IOL including a deformable air chamber according to the invention;

FIG. 1B is a perspective schematic illustration of the accommodative IOL of FIG. 1A in a second configuration according to the invention;

FIG. 2A is a cross-sectional schematic illustration of the accommodative IOL configuration of FIG. 1A;

FIG. 2B is a cross-sectional schematic illustration of the accommodative IOL configuration of FIG. 1B;

FIG. 3A is a perspective schematic illustration of another accommodative IOL including a deformable air chamber according to the invention;

FIG. 3B is a perspective schematic illustration of the accommodative IOL of FIG. 3A in a second configuration according to the invention;

FIG. 4A is a cross-sectional schematic illustration of the accommodative IOL configuration of FIG. 3A;

FIG. 4B is a cross-sectional schematic illustration of the accommodative IOL configuration of FIG. 3B;

DETAILED DESCRIPTION

Figure 5A:
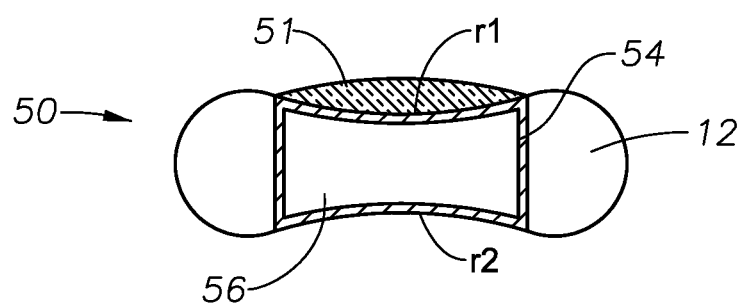
FIG. 5A is a cross-sectional schematic side view of yet another embodiment of an accommodative IOL with a deformable air chamber (and an auxiliary optic) according to the invention.

Certain exemplary embodiments will now be described to provide an overall understanding of the principles of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In one form, the Gaussian lens equation (for variable media) can be written as follows:

$$\frac{n}{s} + \frac{n''}{s''} = \frac{n''-n}{r_1} + \frac{n''-n'}{r_2} = \frac{tc(n'-n)(n''-n')}{n'r_1 r_2}$$

where s is the object distance from the lens, s" is the image distance from the lens, tc is central lens thickness and the first surface of radius (r1) is separating a first medium of refractive index (n) from a second medium of refractive index (n') and the second surface of radius (r2) is separating the second medium (n') from a third medium of refractive index (n").

The above equation can be used for a case where an air lens is disposed within the environment of the eye. In this case, the index (n) of the aqueous fluid on one side of the air chamber as well as the index (n") of the aqueous fluid on the other side of the air chamber are each about 1.34 while the refractive index (n') for air within the lens chamber is substantially lower (n=1.0).

In this embodiment, the lens structure according to the invention is a bubble of air inside lens capsule of the eye, which is otherwise filled with aqueous humor. By employing the general equation above, it is noted that the terms (n'−n) and (n"−n') are both reversed in sign from a typical case, where (n') is the highest index, such as a simple glass lens in air. As a consequence, the focal length of the lens also has a changed sign from the typical case. However, the sign is reversed again by simply changing the sign of the radius of curvatures of the two surfaces.

Thus, a biconcave low index air lens that is immersed in a higher index medium behaves like a converging lens. According to the invention, a converging concave (or preferably biconcave) lens is built out of air and configured to be placed within the higher refractive index environment of the eye as a replacement for the natural lens to provide the same degree of accommodation (nominally from about 14 to about 30 Diopters depending upon the individual).

Additionally, because the air chamber is deformable, radial forces exerted by the cilliary processes on the capsule can be used to change the shape of the air chamber. By changing the curvature of the front or anterior surface (closest to the pupil), the rear or posterior surface (closest to the retina) or both, the overall power of the lens can also be modified to provide focal accommodation.

In FIG. 1A an accommodative IOL device 10 according to the invention is shown including a flexible shell 14 defining an air chamber and a haptic 12 that at least partially surrounds the air chamber. FIG. 1B shows the device 10 of FIG. 1A in a second configuration in which the haptic has been flatten (elongated in a radial direction) causing a deformation of the flexible shell 14.

FIGS. 2A and 2B provide cross-sectional views of the configurations of FIGS. 1A and 1B, respectively. The flexible shell 14 of the air chamber has an anterior surface with a radius of curvature $r_1$ and a posterior surface with a radius of curvature $r_2$. Flattening of the IOL device 10 causes an increase in both radii of curvature, e.g., less concavity, thereby reducing the overall converging power of the air lens.

In FIG. 3A an alternative accommodative IOL device 30 according to the invention is shown including a flexible shell 34 defining an air chamber 36 and a haptic 32 that partially surrounds the air chamber. FIG. 3B shows the device 30 of FIG. 3A in a second configuration in which the haptic has again been flatten (elongated in a radial direction) causing a deformation of the flexible shell 34.

FIGS. 4A and 4B provide cross-sectional views of the configurations of FIGS. 3A and 3B, respectively. The flexible shell 34 of the air chamber 36 has an anterior surface with a radius of curvature $r_1$ and a posterior surface with a radius of curvature $r_2$. Flattening of the IOL device 30 again causes an increase in both radii of curvature, e.g., less concavity, thereby reducing the overall converging power of the air lens.

Figure 5B:
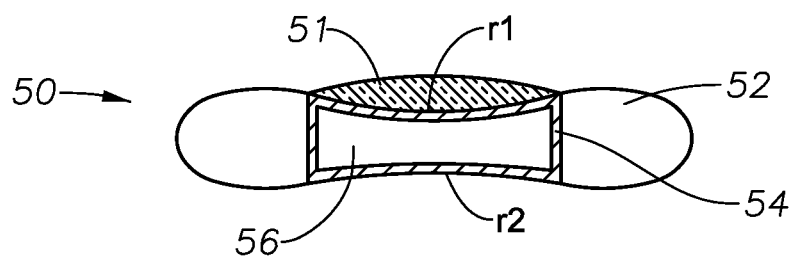
FIG. 5B is a cross-sectional schematic side view of the accommodative IOL of FIG. 5A in a second configuration.

FIGS. 5A and 5B provide cross-sectional views of yet another alternative accommodative IOL device 50 according to the invention again including a flexible shell 54 defining an air chamber 56 and a haptic 52 that at least partially surrounds the air chamber. In the device of FIGS. 5A and 5B, a second optic 51 of conventional construction is used to supplement the converging power of the air lens. Because $r_1$ is now fixed (by coupling of the anterior surface of the flexible shell 54 to solid lens 51), flattening of the IOL device 50 causes an increase in radius of curvature $r_2$ only, as shown in cross-sectional view 5B, which nonetheless reduces the overall converging power of the air lens.

It should be clear that other dual optic configurations can likewise be readily implemented by those skilled the art. A convention lens can be disposed on the posterior surface of the deformable shell 54 (alone or in tandem with the anterior lens 51). Additionally, the power of one or both lens can be negative or positive by appropriate lens shape choices.

For additional details on air lens structures, see, U.S. Pat. No. 6,785,061 issued to Smith on Aug. 31, 2004; U.S. Pat. No. 6,473,238 issued to Daniell on Oct. 29, 2002; both of which are incorporated by reference in their entirety. All of the embodiments described above are non-limiting examples of the present invention only. In addition, all papers and publications cited herein are hereby incorporated by reference in their entirety. One of skill in the art will appreciate further features and advantages of the invention based on the above-described embodiments. Accordingly, the invention is not to be limited by what has been particularly shown and described, except as indicated by the appended claims.

What is claimed is:

1. An accommodative intraocular lens (IOL) system for insertion into an eye to provide accommodative vision, the system comprising:
   a flexible shell having an anterior concave surface and a posterior concave surface defining a deformable air chamber;
   a transparent, low refractive index medium disposed within the shell, wherein the transparent medium has an index of refraction less than 1.2; and
   at least one ring-shaped haptic connected to the shell, the at least one haptic comprising a plurality of spaced-apart and distinct arcuate sections such that the flexible shell is only partially surrounded, each arcuate section connecting to at the anterior surface of the flexible shell at a first anterior portion of the respective arcuate section and at the posterior surface of the flexible shell at a second posterior portion of the respective arcuate section spaced apart from the first portion and configured to facilitate changes in the shape of the air chamber when the haptic is flattened by axially moving the first portion toward the second portion, such that when the lens system is positioned in an eye, ciliary muscle movements can alter the curvature of the anterior and posterior surfaces and vary the overall lens power of the system,
   wherein the transparent medium comprises a gas,
   wherein each of the anterior concave surface and posterior concave surface has a radius of curvature, and wherein flattening of the haptic causes an increase in both radii of curvature,
   wherein the air chamber is configured to form a convergent lens for light entering the anterior surface and exiting the posterior surface when disposed within an aqueous environment, and wherein flattening of the haptic reduces the overall converging power of the convergent lens.

2. The lens system of claim 1, wherein the transparent medium has an index of refraction less than 1.1.

3. The lens system of claim 1, wherein the transparent medium comprises air.

4. The lens system of claim 1, wherein the transparent medium comprises argon.

5. The lens system of claim 1, wherein the transparent medium comprises at least 90 percent argon.

6. The lens system of claim 1, wherein a range of haptic displacement provides an accommodation of at least 3 diopters in an aqueous environment by deformation of the flexible shell.

7. The lens system of claim 1, wherein a range of haptic displacement provides an accommodation of at least 4 diopters in an aqueous environment by deformation of the flexible shell.

8. The lens system of claim 1 wherein the overall optic power of the system is at least 18 Diopters for light entering the anterior surface and exiting the posterior surface when disposed within an aqueous environment.

* * * * *